United States Patent [19]

Webb et al.

[11] 4,277,377

[45] Jul. 7, 1981

[54] PERFUME COMPOSITIONS CONTAINING DIMETHYL HEPTENONITRILES

[75] Inventors: David Webb, Brentwood; Anthony J. Mills, London, both of England

[73] Assignee: Bush Boake Allen Limited, London, England

[21] Appl. No.: 131,632

[22] Filed: Mar. 19, 1980

[30] Foreign Application Priority Data

Mar. 22, 1979 [GB] United Kingdom ............... 10195/79

[51] Int. Cl.³ .................... C07B 120/00; A61K 7/46
[52] U.S. Cl. ........................... 252/522 R; 260/465.9
[58] Field of Search .................................. 252/522 R

[56] References Cited

U.S. PATENT DOCUMENTS

| | | | |
|---|---|---|---|
| 3,325,369 | 6/1967 | Somerville | 252/522 R |
| 3,553,110 | 1/1971 | Mitchell | 252/522 R |
| 3,960,923 | 6/1976 | DeSimone | 252/522 R |
| 4,156,690 | 5/1979 | DeSimone | 252/522 R |

FOREIGN PATENT DOCUMENTS 1078286  8/1967 United Kingdom .
1508008  4/1978 United Kingdom .
1523028  8/1978 United Kingdom .

*Primary Examiner*—John F. Niebling
*Attorney, Agent, or Firm*—Frishauf, Holtz, Goodman & Woodward

[57] ABSTRACT

Compounds of the formula:

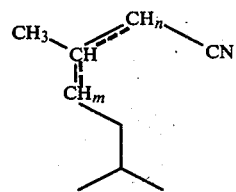

wherein n and m are integers having a value of 1 or 2 and n+m=3 and the dashed line indicates two alternative positions of a unit of unsaturation are novel. They possess attractive spicy odors and are useful as ingredients of compounded perfumery compositions. They are readily prepared by the reaction of methyl iso-amyl ketone and cyano-acetic acid.

5 Claims, No Drawings

PERFUME COMPOSITIONS CONTAINING DIMETHYL HEPTENONITRILES

This invention relates to novel organic chemicals to method for their preparation and to compounded perfumery compositions, containing them.

From one aspect the invention provides compounds having the formula I.

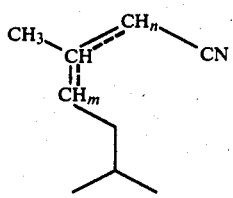

wherein, n and m are integers having a value of 1 or 2, n+m=3 and the dashed line indicates the two alternative positions of a single unit of unsaturation. Such compounds may be individual isomers having the above formula or be mixtures of such isomers.

These compounds have been discovered to possess attractive odours having distinctive spicy note reminiscent of cummin oil. They are suitable for blending with a wide range of odiferous chemicals of synthetic or natural origin to produce a compounded perfumery composition having a characteristic attractive odiferous quality.

The perfumery compositions to which this invention relates are those where a number of odiferous materials of synthetic or natural origin are admixed or compounded to form a perfumery concentrate. Such concentrates may find use before or after dilution but more usually they are added in small proportions to other materials such as space sprays or to soap detergent cosmetic deodorant or toiletry compositions in order to provide them with agreeable olfactory properties. Thus such concentrates are products of commerce and may comprise a simple or complex mixture of individual perfumery compounds.

From another aspect our invention provides a compounded perfumery composition which comprises a plurality of odiferous chemicals together with at least one compound having the formula I.

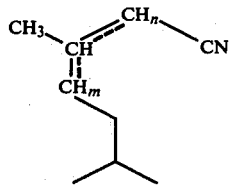

wherein n and m are integers having a value of 1 to 2, m+n=3 and the dashed line indicates the two alternative positions of a single unit of unsaturation.

The novel perfumery compositions may be compounded according to recognised techniques or perfumery employing known odiferous perfumery ingredients, e.g. techniques and ingredients mentioned in the standard textbooks "Soap, Perfumery and Cosmetics" by W. A. Poucher, 7th edition published by Chapman & Hall (London 1959; "Perfume and Flavour Chemicals" by S. Arctander, published by the author (Montclair) 1959 and "Perfume and Flavour Materials of Natural Origin" also by S. Arctander, self-published, Elizabeth NJ, 1960.

Typical perfumery materials which may form part of compounded composition include: natural essential oils such as lemon oil, mandarin oil, clove leaf oil, petitgrain oil, cedar wood oil, patchouli oil, lavandin oil, neroli oil, ylang oil, rose absolute or jasmin absolute; natural resins such as labdanum resin or olibanum resin; single perfumery chemicals which may be isolated from natural sources or manufactured synthetically, as for example alcohols such as geraniol, nerol, citronellol, linalol, tetrahydrogeraniol, betaphenylethyl alcohol, methyl phenyl carbinol, dimethyl benzyl carbinol, menthol or cedrol; acetates and other esters derived from such alcohols; aldehydes such as citral, citronellal, hydroxycitronellal, lauric aldehyde, undecylenic aldehyde, cinnamaldehyde, amyl cinnamic aldehyde, vanillin or heliotropin; acetals derived from such aldehydes; ketones such as methyl hexyl ketone, the ionones and the methylionones; phenolic compounds such as eugenol and isoeugenol; synthetic musks such as musk xylene, musk ketone and ethylene brassylate; and other materials commonly employed in the art of perfumery. Typically at least five, and usually at least ten, of such materials will be present as ingredients of the compounded composition.

Particularly preferred odiferous ingredients for blending with the compounds of this invention include, eugenol, iso-eugenol, aldehyde $C_{11}$, bergamot oil, amyl salicylate, parchouli oil, oakmoss and lavandin oil.

The novel compounds of the invention (hereinafter for convenience termed dimethyl hepteno-nitriles) may form a major part of a compounded perfumery but preferably they will form a minor part of the compounded compositions e.g. from 0.1 to 25 parts by weight more preferably from 0.5 to 15 parts by weight of one or more of the dimethyl hepeno-nitriles being employed.

Mixtures of the various isomeric dimethyl heptenonitriles having the general formula I as defined above are useful according to our invention. For each compound wherein n and m are fixed there are two geometrical isomers which are normally produced concurrently during the preparation. Especially preferred for present use are the two geometrical isomers of the nitrile of formula I wherein n has a value of 1 and m has a value of two.

The novel hepteno-nitriles of this invention are readily prepared using the conventional techniques of synthetic organic chemistry. Conveniently they are prepared by reacting methyl isoamyl ketone i.e. the compound.

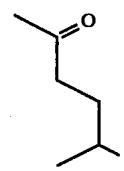

with acetonitrile in the presence of a strong base or preferably by reaction with cyano-acetic acid and subsequently decarboxylating the cyano-carboxylic acid which is formed.

This latter reaction is preferably carried out by mixing methyl iso-amyl ketone with at least an equimolar quantity of cyanoacetic in a suitable inert solvent such as toluene, xylene or ethylbenzene. An excess of cyanoacetic acid is preferably present e.g. 5 or 10% on a molar basis. A catalytic quantity of a suitable catalyst e.g. ammonium acetate or p-toluene sulphonic acid is preferably present. The reaction proceeds via the formation of an intermediate cyano-carboxylic acid which undergoes decarboxylation to form the desired dimethyl heptenonitriles. The intermediate cyano-carboxylic acid is formed at ambient temperatures. This intermediate can be isolated as the decarboxylation is very slow at ambient temperatures. Preferably the decarboxylation is effected by heating the cyano-carboxylic acid intermediate to a temperature of from 40° to 180° C. more preferably 140° to 180° C. for a period of from 5 to 10 hours. We prefer to react the methyl iso-amyl ketone and cyano acetic acid at such temperatures so as to generate the cyano-carboxylic acid as a transient intermediate. If it is preferred to use a solvent which has a higher boiling point than the temperature at which decarboxylation is to be effected for the reaction of the ketone and cyano-acetic acid and this is a necessity temperature at which decarboxylation is to be effected for the reaction of the ketone and cyano-acetic acid and this is a necessity where this reaction is to be carried out at the same temperature as is used for the decarboxylation.

The product of this reaction can be separated by fractional distillation. Conveniently a single fraction which comprises a mixture of the novel hepteno-nitriles can be separated. When the reaction between methyl-amyl ketone and cyanoacetic acid is carried out under the preferred conditions described above such a mixture will comprise a predominent proportion of the preferred nitrile i.e. the compound having the formula I, wherein n has a value of 1 and m has a value of 2. Mixtures of the two nitriles can be separated but preferably they are employed directly as ingredients of compounded perfumery compositions.

The invention is illustrated by the following Examples:

EXAMPLE 1

114 gm of methyl iso-amyl ketone, 94 gm of cyanoacetic acid, 136 gm of toluene and 4 gm of ammonium acetate were charged to a 1 liter flask and heated to reflux the water formed being taken off. The product was washed three times with brine and stripped of solvent. It was then stirred at 140° C. for a period of 34 hours so as to effect decarboxylation. Distillation yielded 87 gm of product boiling at 76° to 78° C. c/5 mm Hg. This distillate comprised a mixture of the four possible isomers of compounds having the formula I. Its odour has a spicy-cumminic note with citrus undertones.

EXAMPLE 2

FOUGERE TYPE FRAGRANCE

Dimethyhepteno nitrile (product of Example 1)—0.5 gm
Geranium oil (bourbon)—0.5 gm
Lavandin oil—0.8 gm
Bergamot oil—0.8 gm
Clove stem oil—0.3 gm
Cedarwood oil(Virginian)—0.3 gm
Patchouli oil—1.0 gm
Amyl salicylate—1.0 gm
Musk ambrette—1.0 gm
Oakmoss absolute (50% in DPG)—0.5 gm

We claim:

1. A compounded perfumery composition which comprises a plurality of odiferous chemicals together with at least one compound having the formula I.

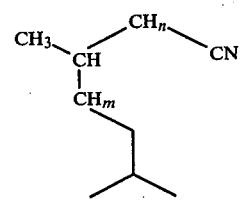

wherein n and m are integers having a value of 1 or 2, m+n=3 and the dashed line indicates alternative positions for a single unit of unsaturation.

2. A composition according to claim 1, wherein the compound of formula I is that where n=1 and m=2.

3. A composition according to claim 1 which comprises from 0.1 to 25 parts by weight of a compound of the formula I.

4. A composition according to claim 3 which comprises from 0.5 to 15.0 parts by weight of a compound of formula I.

5. A composition according to claim 1 which comprises one or more odiferous ingredients selected from the group consisting of eugenol, iso-eugenol, aldehyde $C_{11}$, bergamot oil, amyl salicylate, patchouli oil, oakmoss and lavandin oil.

* * * * *